United States Patent
Bihler et al.

(10) Patent No.: US 10,426,948 B2
(45) Date of Patent: Oct. 1, 2019

(54) EXTENDABLE ELECTRODE

(71) Applicant: BIOTRONIK SE & Co. KG, Berlin (DE)

(72) Inventors: Eckardt Bihler, Winterthur (CH); Marc Hauer, Uster (CH)

(73) Assignee: BIOTRONIK SE & Co. KG, Berlin (DE)

( * ) Notice: Subject to any disclaimer, the term of this patent is extended or adjusted under 35 U.S.C. 154(b) by 14 days.

(21) Appl. No.: 15/359,787

(22) Filed: Nov. 23, 2016

(65) Prior Publication Data

US 2017/0165473 A1   Jun. 15, 2017

(30) Foreign Application Priority Data

Dec. 15, 2015   (DE) .................. 10 2015 121 817

(51) Int. Cl.
*A61N 1/05*   (2006.01)

(52) U.S. Cl.
CPC .............. *A61N 1/05* (2013.01); *A61N 1/0551* (2013.01)

(58) Field of Classification Search
CPC ........................................................ A61N 1/05
See application file for complete search history.

(56) References Cited

U.S. PATENT DOCUMENTS

| | | | |
|---|---|---|---|
| 5,522,874 A | 6/1996 | Gates | |
| 7,617,004 B2 * | 11/2009 | Bartels | A61N 1/0563 607/116 |
| 8,768,490 B2 * | 7/2014 | Weitzig | A61N 1/056 607/122 |
| 9,393,404 B2 * | 7/2016 | Decre | A61N 1/0551 |
| 2003/0216800 A1 | 11/2003 | Ebert et al. | |
| 2006/0074470 A1 | 4/2006 | Bartels et al. | |
| 2008/0027524 A1 | 1/2008 | Maschino et al. | |
| 2008/0039896 A1 | 2/2008 | Osypka | |
| 2009/0125089 A1 * | 5/2009 | Bischoff | A61N 1/0551 607/116 |
| 2009/0210040 A1 | 8/2009 | Ochoa | |
| 2009/0281608 A1 | 11/2009 | Foster | |
| 2010/0114279 A1 * | 5/2010 | Strandberg | A61N 1/05 607/116 |
| 2010/0331934 A1 | 12/2010 | McDonald et al. | |
| 2012/0158097 A1 | 6/2012 | Weiss et al. | |
| 2012/0158109 A1 | 6/2012 | Bartels et al. | |
| 2013/0158638 A1 | 6/2013 | Zhulati et al. | |

FOREIGN PATENT DOCUMENTS

WO   9417852 A1   8/1994

OTHER PUBLICATIONS

European Search Report and Annex to the European Search Report on European Patent Application No. EP 16 19 9801.8, dated Feb. 16, 2017 (8 pages).
German Search Report for German Case No. DE 10 2015 121 817.8, dated Jun. 24, 2016 (8 pages).

* cited by examiner

*Primary Examiner* — Eric D. Bertram

(74) *Attorney, Agent, or Firm* — Buchanan Ingersoll & Rooney PC

(57) ABSTRACT

An implantable electrode having a connection portion. So as to be able to easily stretch the electrode lengthwise, provision is made so that the connection portion is embodied in a coiled manner.

9 Claims, 4 Drawing Sheets

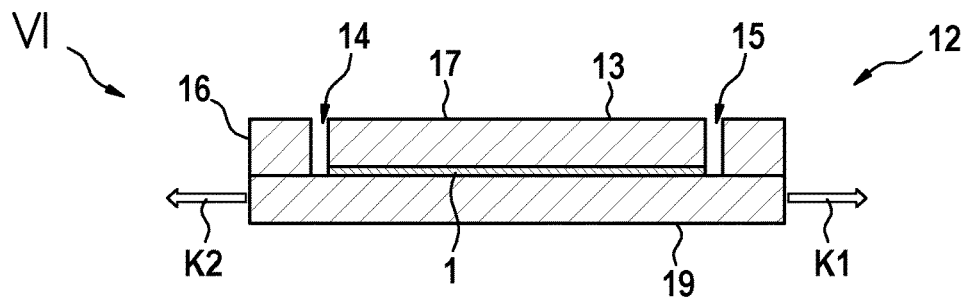
FIG. 6
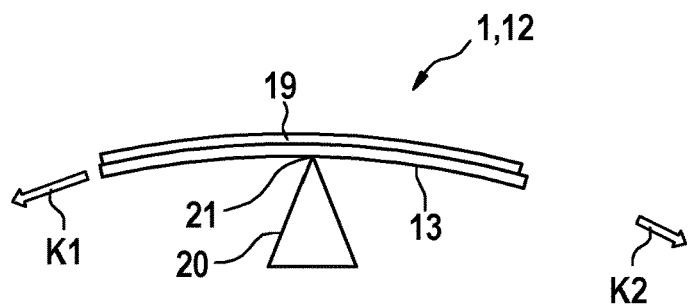
FIG. 7
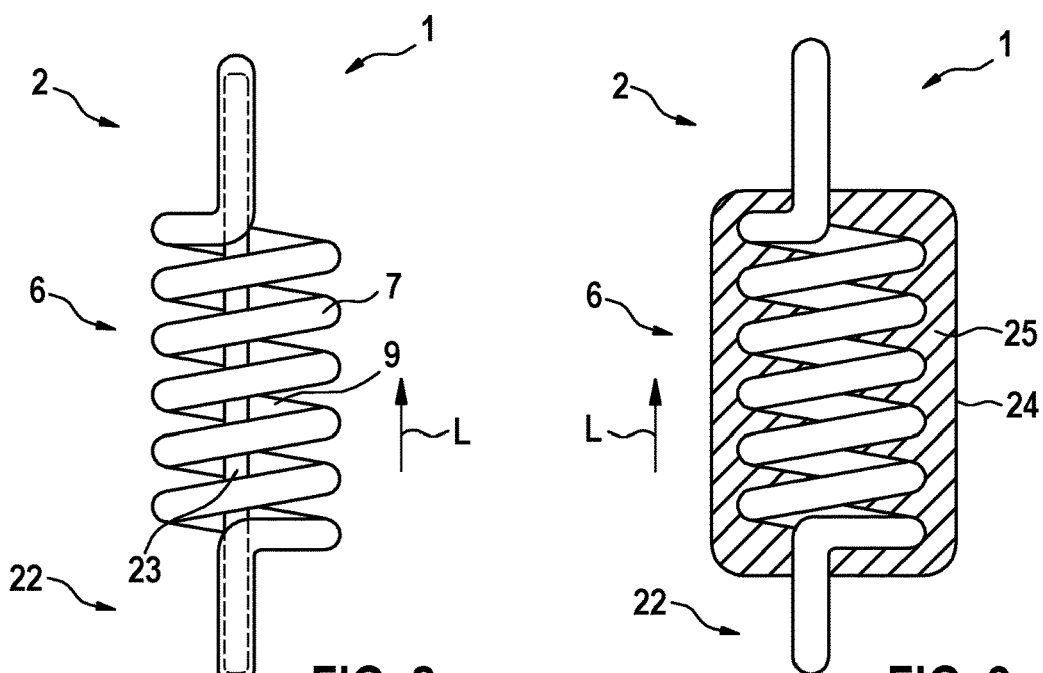
FIG. 8
FIG. 9

EXTENDABLE ELECTRODE

CROSS-REFERENCE TO RELATED APPLICATIONS

This patent application claims the benefit of and priority to co-pending German Patent Application No. DE 10 2015 121 817.8, filed Dec. 15, 2015 in the German Patent Office, which is hereby incorporated by reference in its entirety.

TECHNICAL FIELD

The present invention relates to an implantable electrode having a contact element for contacting bodily tissue, for example, muscle cells of the heart or nerve ends, and having a connection portion for connecting a medical device, for example, a pacemaker, to the contact element. The present invention also relates to a method for producing an implantable electrode having a contact element for contacting bodily tissue, and having a connection portion for connecting a medical device to the contact element.

BACKGROUND

Implantable electrodes and methods for production thereof are known in general. Implantable electrodes are often flexible and easily pliable transversely to their longitudinal axis. However, the electrodes are substantially non-extendable along the longitudinal axis, with known electrodes being less than 1% extendable along the longitudinal axis, for example.

The present invention is directed toward overcoming one or more of the above-mentioned problems.

SUMMARY

An object of the present invention is therefore to provide an implantable electrode and a method for producing an implantable electrode, wherein the implantable electrode is extendable, at least in one or more portions, along its longitudinal axis.

For the electrode mentioned in the introduction, at least the object is achieved in that the connection portion winds at least in part around the longitudinal axis of the electrode. For the method mentioned in the introduction, at least the object is achieved in that the connection portion has been wound at least in part around an axis. Since the connection portion is formed in a wound manner at least in part, the electrode and in particular the connection portion thereof can be extended easily along the longitudinal axis, i.e., can be pulled apart from itself, even if the connection portion per se is not resiliently extendable.

A solution according to the present invention can be further improved by various embodiments, which are each advantageous per se and, unless otherwise specified, can be combined with one another arbitrarily. Reference will be made hereinafter to these embodiments and the advantages associated therewith.

The connection portion may thus comprise at least one part-turn, at least one entire turn, or more than one turn. The more turns the connection portion has, the easier can the connection portion be pulled apart from itself along the longitudinal axis. The maximum possible extension of the connection portion along the longitudinal axis can also become greater with the increasing number of turns. By way of example, the connection portion is formed helically at least in part. The helix is a comparatively regular structure which can be easily produced.

A shape encasing the wound part of the connection portion can correspond substantially to a cylinder when the longitudinal axis runs in a straight line and the electrode is not bent transversely to the longitudinal axis. If the electrode is bent, the encasing shape can correspond to a tube. Due to the substantially cylindrical or tubular encasing, no parts of the connection portion protrude beyond other parts of the connection portion and, therefore, the connection portion can be easily implanted.

The connection portion can be formed as a flat ribbon wound around the longitudinal axis. The flat ribbon can also form the contact portion of the electrode supporting at least one contact element. A flat ribbon can be wound more easily than a round cable, for example, which might possibly form folds on an inner side of the turn.

In accordance with one embodiment of the method according to the present invention, the connection portion can be formed flat and the at least one connection line can be embedded in a flat casing. The flat casing can be brought into the wound form with the at least one embedded connection line. For example, the casing can be formed as a flat ribbon cable, wherein the at least one connection line is arranged between two electrically insulating films, in particular thermoplastic polymer films, for example, formed from a liquid-crystal polymer. In particular, one of the films can be provided on one of its sides with the at least one connection line. On the side of this film opposite the connection line, the film can be provided with the at least one contact element. The connection line and/or the contact element can be applied additively or subtractively to the film. In order to be able to bring the connection line and the contact element into connection with one another, a plated through-hole can be provided, which can be formed as what is known as a metallised via. A via is, for example, a metallised opening in the film, connecting the two sides of the film to one another.

The connection portion and, in particular, the wound flat casing thereof, can have broad and narrow sides, wherein one of the broad sides is an outer side pointing away from the longitudinal axis. The outer side is preferably flat and makes it possible, in particular, for the wound part of the connection portion to slide easily with contact against tissue during the implantation, without becoming hooked on said tissue. This electrode therefore can be easily implanted.

In order to be able to provide the turn permanently, the outer side can be larger than an inner side, facing towards the longitudinal axis, of the connection portion and, in particular, of the wound flat casing.

The outer side can be plastically deformed and, for example, stretched to a greater extent than the inner side. The greater stretching of the outer side can be easily generated mechanically.

The outer side may have been mechanically extended and at the same time thermally treated in order to generate the larger outer side. The combination of mechanical extension or stretching and thermal treatment enables the enlargement and, for example, plastic extension of the outer side with low mechanical forces, such that damage to the electrode is avoided and production waste is reduced.

Alternatively or additionally to the enlarged design of the outer side, the connection portion and, in particular, the wound flat casing thereof can be provided with a coating exerting a mechanical stress onto the connection portion in order to produce the turn. If the coating is applied to the outer side of the wound connection portion, the coating can be designed to produce a compressive stress. A coating applied to the inner side of the wound connection portion can be designed to produce a tensile stress. The outer side and/or the inner side can each be provided with a coating.

It is possible for the contact portion to not be wound and to be substantially flat in an un-deformed state, in which it lies, for example, on a flat surface.

In accordance with one embodiment of the method according to the present invention, the connection portion can be wound around a cylindrical mold, for example, a cylindrical core. Individual turns, or all turns, in the wound form can be secured to at least one neighbouring turn in order to permanently maintain the wound form. Furthermore, individual turns, or all turns, can be fastened to the core. In order for the electrode and, in particular, the connection portion thereof with a core which is fixed to the turns, to be tensile lengthwise, the core can be flexible along the longitudinal axis of the electrode. Alternatively, the core can serve as a tool around which the connection portion and, in particular, the casing thereof is wound, wherein the core is removed from the wound part of the connection portion once the wound part has been formed.

The core is preferably cylindrical or hollow-cylindrical and, for example, tubular. The core can prevent the casing from buckling in the event of a possible excessive bending, i.e., with an excessively small bending radius, and can prevent any edges or corners produced in the buckled area from hindering the implantation of the electrode.

The casing can be connected to the core in an integrally bonded manner and, for example, by fusion, whereby the connection between casing and core can be formed without any further auxiliaries, for example, adhesives or seams.

The core can be formed with a lumen extending continuously through the core along the longitudinal axis of the electrode so that the electrode can be implanted for, example, with the aid of a guide wire, which guides the electrode during implantation. If the electrode is formed without a core, the wound casing of the connection portion can provide the lumen.

The material of the casing can be a thermoplastic polymer, for example, a liquid-crystal polymer. The core can be manufactured, for example, from glass or also from a polymer, for example, from a liquid-crystal polymer, and can even consist thereof. The connection line, for example, consists of gold or of a gold alloy. The at least one contact element can be manufactured from gold, from a gold alloy, or, for example, from a platinum-iridium alloy.

The film can be placed around the core together with the at least one contact element and the at least one connection line. Alternatively or additionally, a further film can be placed onto the side of the film comprising the connection line. In particular, when the films are thermoplastic polymer films, the two films can be thermally connected to one another permanently, and for example, can be fused to one another.

So as to be able to wind the casing with the aid of the core, the casing can first be placed around the core, wherein the casing hugs the core, in particular, along the peripheral direction of said core and can surround the core at least in part or even entirely.

If the casing is to be easily fastened to the core, the casing and the core can be connected to one another in an integrally bonded manner. In particular, if both the casing material and the core are manufactured from a thermoplastic polymer material, the casing and the core can be easily fastened to one another under the influence of temperature and pressure and, for example, can be fused to one another. For example, the casing can be pressed by a mold against the core, wherein the mold preferably does not adhere to the casing and, for example, has Teflon or ceramic surfaces, which contact the casing during the production of the electrode. So as to be able to fasten the casing to the core, the casing and core can be heated to 350° C. and, for example, to 200° C. These temperatures can be maintained for up to 20 minutes and, for example, for at least 1 second. The material of the casing and core can be fused with one another during a temperature treatment of this type and can thus be connected to one another in an integrally bonded manner seamlessly or at least practically seamlessly.

By way of example, polyurethane or another polymer can be used as liquid-crystal polymer.

In the state wound around the cylindrical mold and/or the ore the wound connection portion can be heated. By way of example, this heating or temperature control can be temporary, and may last, for example, for 1 second. The heating process, however, can absolutely last for a number of minutes and, for example, up to 10 minutes, up to 30 minutes, or even up to 60 minutes. Temperatures of the wound connection portion can be up to 150° C., or even up to 250° C., or even up to 350° C. during the thermal treatment.

By way of example, the heating can be performed with the aid of a hot airflow directed onto the outer side of the wound connection portion. As a result, the outer side can be heated to a greater extent than the inner side, in particular, when the heating lasts only for a short period of time, that is to say less than up to 60 seconds, for example.

Alternatively, the connection portion and, in particular, the casing thereof can be drawn over an edge in a manner pressing against the edge in order to permanently stretch the outer side. The connection portion and, in particular, the casing thereof preferably bears here with its inner side against the edge. In addition to the shaping with the aid of the edge, the connection portion can be heated. The edge can thus be part of a heatable tool. Alternatively, the hot airflow can be directed onto parts of the connection portion. In particular, the hot airflow can be directed onto parts of the connection portion still to be drawn over the edge or parts of the connection portion already bearing against the edge.

Alternatively or additionally to the mechanical and/or thermal shaping of the wound connection portion, the connection portion can be provided at least on one side with a coating exerting mechanical stress onto the conductor portion. The stress can be a compressive stress or a tensile stress. If the mechanical stress is a compressive stress, the coating twists the connection portion such that the coated side forms the outer side of the connection portion. If the mechanical stress is a tensile stress, the coating twists the connection portion such that the coated side forms the inner side. The stress thus twists the connection portion and, in particular, the casing thereof.

Each of the connection lines can be electrically conductively connected to a separate contact element. It can be sufficient for the electrode to have two or three connection lines and contact elements, for example, when the electrode is designed to connect a cardiac pacemaker or defibrillator to the heart. Alternatively, the electrode can have more than three and, for example, up to 10, 20, 30, 40, 50 or even more than 50 connection lines and contact elements.

Further embodiments, features, aspects, objects, advantages, and possible applications of the present invention could be learned from the following description, in combination with the Figures, and the appended claims.

The electrode according to the present invention can be produced in accordance with the method according to the present invention. The electrode according to the present invention can be produced by means of the method according to the present invention.

DESCRIPTION OF THE DRAWINGS

The present invention will be explained hereinafter by way of example on the basis of embodiments with reference to the drawings. The different features of the embodiments can be combined here independently of one another, as has already been presented in the advantageous embodiments. In the drawings:

FIGS. 5-6 show a preliminary product of an exemplary embodiment of the implantable electrode, FIG. 7 shows the preliminary product or FIGS. 5-6 with a stretching tool, FIGS. 8-9 show two exemplary embodiments of connection portions of the electrode according to the present invention.

DETAILED DESCRIPTION

Firstly, the structure and function of an implantable electrode according to the present invention will be described with reference to the exemplary embodiment of FIG. 1.

Figure 1:
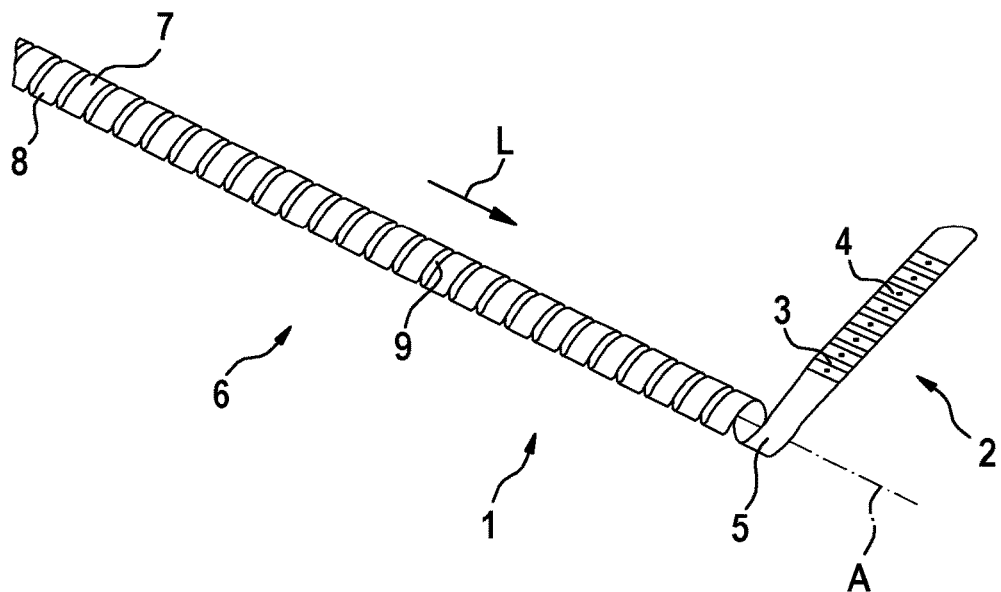
FIG. 1 shows a schematic perspective illustration of an exemplary embodiment of the implantable electrode according to the present invention.

FIG. 1 shows the implantable electrode 1 schematically in a perspective view. In particular, FIG. 1 shows a distal end of the electrode 1. The distal end is formed as a contact portion 2 with a contact side 3. The contact portion 2 has, at least on the contact side 3, at least one contact element 4, which in the implanted state of the electrode 1 electrically contacts bodily tissue and, for example, muscle or nerve cells. In FIG. 1, the electrode 1 is provided by way of example with eight contact elements 4, which are all arranged on one contact side 3.

The contact elements 4 are arranged on a casing 5 of the electrode 1. Connection lines, which are electrically conductively connected to the contact elements 4, are disposed inside the casing 5. Since the connection lines are embedded in the casing 5, they are not illustrated in FIG. 1. The connection lines serve to electrically connect the contact elements 4 to a medical device, for example, a pacemaker or a defibrillator, and extend through the electrode 1 and, in particular, through the casing 5. A connection portion 6 of the electrode 1 adjoining the contact portion 3 guides the connection lines to the medical device. If the electrode 1 has a connection end opposite the distal end, the connection portion 6 is thus arranged between the distal end and the connection end. The connection end serves to connect the electrode 1 to the medical device, for example, a defibrillator, a cardiac pacemaker or another medical device, for example, for nerve stimulation.

The connection portion 6 is wound and is illustrated with a multiplicity of turns. By contrast, it is possible that the contact portion 2 is not wound and, in particular, can be flat. On account of the wound form of the connection portion 6, this is extendable along a longitudinal direction L of the connection portion 6, i.e., is tensile lengthwise. A longitudinal axis A of the connection portion 6 extends along the longitudinal direction L, wherein the casing 5 is wound around the longitudinal axis. Since the longitudinal axis A is surrounded by the turns of the connection portion 6, it has been illustrated only in part for the sake of simplicity.

The connection portion 6 and, in particular, the turns thereof have an outer side 7, which points away from the longitudinal axis A and which can be oriented parallel to the longitudinal direction L. If the casing 5 of the connection portion 6 or the electrode 1 as a whole is formed flat, the outer side 7 can thus be a broad side of the connection portion 6. A narrow side 8 of the wound casing 5 can be arranged pointing in or against the longitudinal direction L. The turns can be arranged in succession in the longitudinal direction L and can be substantially aligned with one another so that none of the turns significantly protrude beyond any of the other turns transversely to the longitudinal direction L.

Opposite the outer side 7, the wound casing 5 of the connection portion 6 can have an inner side 9. The inner side 9 can be substantially flat, similarly to the outer side 7, such that the casing 5 is formed as a flat ribbon at least in the region of the connection portion 6 or in the region of the electrode 1 as a whole. If the inner side 9 is flat or smooth and extends along the longitudinal axis A, the connection portion 6 can be easily implanted with the aid of a guide wire.

The contact side 3 is provided in the exemplary embodiment of FIG. 1 on the outer side 7. Alternatively, the contact side 3 can be arranged on the inner side 9. Furthermore, contact elements 4 can be arranged both on the outer side 7 and on the inner side 9 when the contact portion 2 is intended to contact tissue on both sides.

Due to the plurality of turns of the connection portion 6, the connection portion 6 and, in particular, the casing 5 thereof can be helical.

In the exemplary embodiment of FIG. 1 the contact portion 2 extends away from the connection portion 6 substantially perpendicularly to the longitudinal direction L. Alternatively, however, the contact portion 2 can also extend in a direction other than that illustrated and, for example, parallel to the longitudinal direction L.

Figure 2:
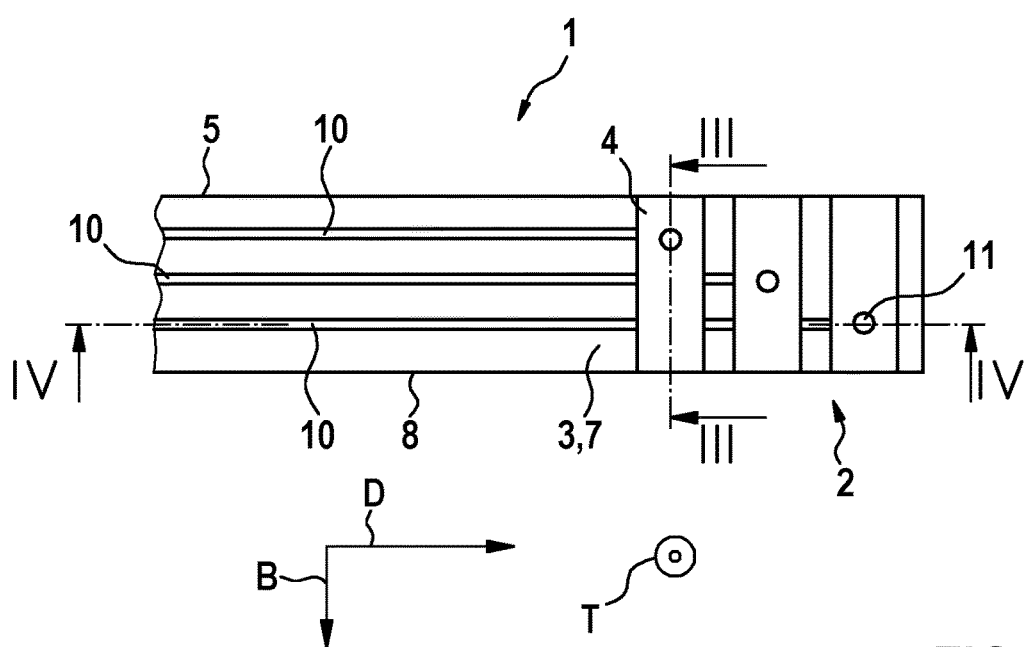
FIGS. 2-4 show schematic illustrations of an exemplary embodiment of a contact portion of the electrode according to the present invention.

FIG. 2 shows a flat casing 10 as semi-finished product of the casing 4 of a further exemplary embodiment of the electrode 1 according to the present invention. The same reference signs are used for elements that correspond in terms of function and/or structure to elements of the exemplary embodiment of FIG. 1. One skilled in the art will appreciate that merely the differences from the exemplary embodiment of FIG. 1 will be discussed hereinafter.

The outer side 7 of the flat casing 5 corresponds to the outer side 7 of the wound connection portion 6. Three strip-like contact elements 4 are arranged on the outer side 7 of the flat casing 5 and are arranged successively and at a distance from one another in a longitudinal direction D of the contact portion 2. The contact elements 5 can cover the outer side 7 fully in a width direction B of the contact portion 2.

Each of the contact elements 4 can be electrically conductively connected to another connection line 10 of the electrode 1. The electrode 1 can thus have three connection lines 10, for example. Each of the connection lines 10 can be electrically conductively connected to one of the contact elements 4 with the aid of another plated through-hole 11.

In the exemplary embodiment of FIG. 2 the connection lines 10 extend only as far as the plated through-hole 11, which electrically conductively connects the corresponding connection line 10 to the corresponding contact element 4. Alternatively, however, the connection lines 10 can also extend in the longitudinal direction D past this plated through-hole 11 and even completely through the contact portion 2. An undesired contacting of one of the connection lines 10 with a different contact element 4 is thus prevented in that the contact element 4 is arranged on the outer side 7 and the connection lines 10 are arranged at a distance from the outer side 7 in a thickness direction T pointing transversely to the longitudinal direction D and to the width direction B.

Figure 3:
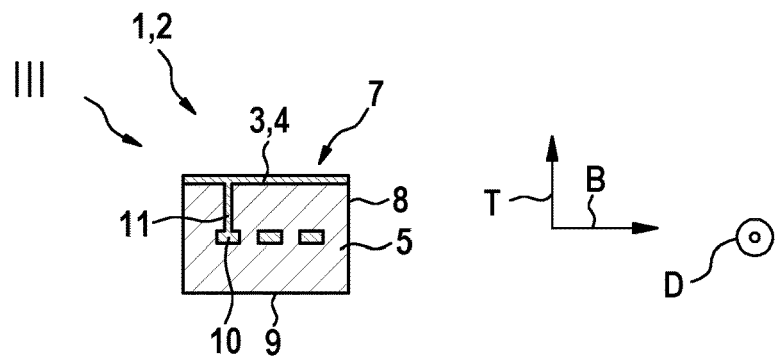

FIG. 3 shows the contact portion 2 of the exemplary embodiment of FIG. 2 schematically in a sectional view III, which extends transversely to the longitudinal direction D through one of the contact elements 4. The longitudinal direction D is directed out of the drawing plane. The connection lines 10 are arranged adjacently and at a distance from one another in the width direction B. The connection lines 10 are provided at a distance from the contact element 4 in the thickness direction T. The plated through-hole 11, which electrically conductively connects the illustrated contact element 4 to one of the connection lines 10, runs in the thickness direction T from the connection line 10 to the contact element 4.

The connection lines 10 can be arranged on the inner side 9 of the casing 5 opposite the outer side 7. In the exemplary embodiment of FIG. 3, however, the connection lines 10 are embedded in the casing 5 so that the connection lines 10 can be contacted transversely to the longitudinal direction D only via one of the contact elements 4 and the corresponding plated through-hole 11.

Figure 4:
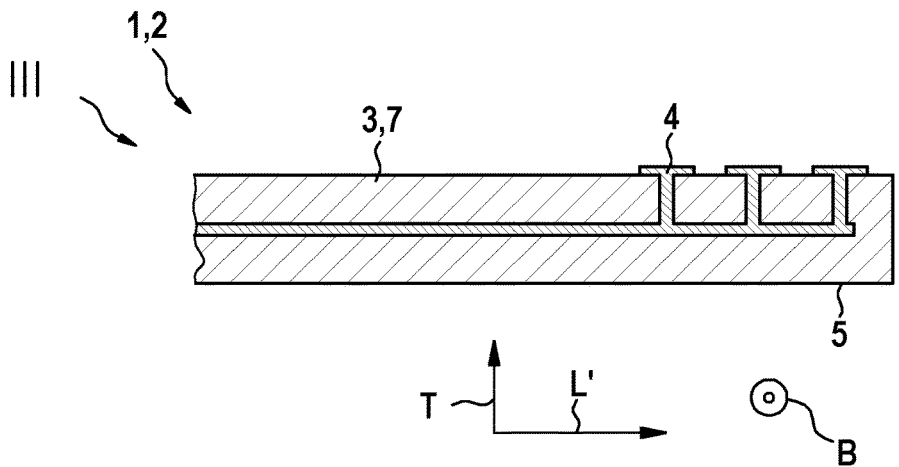

FIG. 4 shows the contact portion 2 of the exemplary embodiment of FIGS. 2-3 in a sectional view IV, wherein the plane of section runs through one of the connection lines 10, i.e., parallel to the longitudinal direction D and to the thickness direction T.

Figure 5:
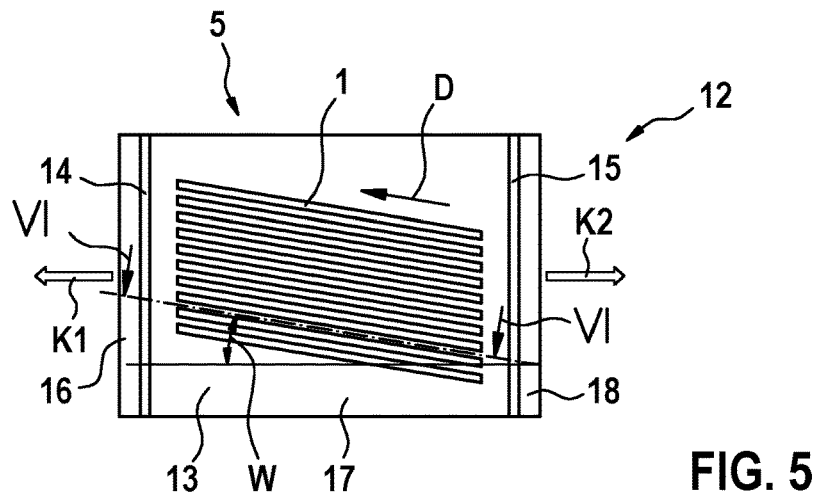

FIG. 5 shows a schematic plan view of a semi-finished product 12 comprising a plurality of implantable electrodes 1. The semi-finished product 12 can comprise fewer than the illustrated number of electrodes 1 and, for example, can comprise at least one electrode 1. The connection lines 10 are arranged between two films 13 forming the casing 5, wherein, in the view of FIG. 5, one of the films is hidden by the film 13. The hidden film is mechanically stretched, which is illustrated by the force arrows K1, K2. The force arrows K1, K2 of the stretching force acting on the film illustrated in a hidden manner point away from one another so that the hidden film is pulled apart from itself, i.e., is stretched. The stretched film can later form the outer side 7 of the electrode 1. The stretching force does not act directly on the film 13 and, therefore, the film 13 is not stretched or is stretched at least to a lesser extent than the hidden film.

In order to be able to mechanically better decouple the hidden film from the film 13, the semi-finished product 12 can be provided with grooves 14, 15 running transversely to the force arrows K1, K2. The grooves 14, 15 can divide the film 13 into different portions 16, 17, 18 running parallel to the grooves 14, 15. The middle portion 17 arranged between the outer portions 16 and 18 comprises the electrodes 1. The electrodes 1 cannot extend as far as the outer portions 16, 18.

In order to ensure that the electrodes 1 after separation are wound helically and not just spirally in one another, the electrodes 1 extend at an angle W to the force arrows K1, K2. The value for the angle W lies preferably between 10 and 60 degrees. Consequently, the longitudinal direction D extends at this angle W to the effective stretching force. The angle W can correspond substantially to the pitch angle of the turns of the helical connection portion 6.

FIG. 6 shows exemplary embodiment of FIG. 5 schematically in a sectional view along the line VI in FIG. 5. As can be seen from FIG. 6, the grooves 14, 15 can extend completely through the film 13 in order to separate the portions 16, 17, 18 thereof completely from one another. The film 19 can also be seen in the view of FIG. 6. The film 19 is stretched by the stretching force to a greater extent than the film 13, as illustrated by the force arrows K1, K2. The stretching is performed plastically. On account of the stretching, the electrodes 1 and, in particular, the connection portions 6 thereof bend, such that the connection portions 6 of the electrodes 1 become helical.

FIG. 7 shows a further exemplary embodiment of an electrode 1 or a semi-finished product 12 during the mechanical stretching of the film 19. The electrode 1 or the semi-finished product 12 is drawn over a stretching tool 20 in order to stretch the film 19 to a greater extent than the film 13. Here, the film 13 is drawn over the stretching tool 20 so as to press against the stretching tool 20 and, in particular, against an edge 21 of the stretching tool 20. This is illustrated by way of example by the force arrows K1, K2, which, in particular, are to be interpreted here as force vectors. The force vectors K1, K2 have components which point towards the edge 21, that is to say which draw the electrode 1 or the semi-finished product 12 towards the edge 21. The force vector K1 is also greater than the force vector K2 and, therefore, the electrode 1 or the semi-finished product 12 is drawn over the edge 21 substantially in the direction of the force vector K1.

FIG. 8 shows a further exemplary embodiment of the implantable electrode 1 in a schematic side view. The same reference signs are used for elements which correspond in terms of function and/or structure to elements of the previous exemplary embodiment. One skilled in the art will appreciate that merely the differences from the previous exemplary embodiments will be discussed hereinafter for the sake of brevity.

The connection portion 6 is coiled as in the previous exemplary embodiments, i.e., is illustrated as being helical. The electrode 1 of the exemplary embodiment of FIG. 8 is also illustrated with the contact portion 2, which extends parallel to the longitudinal direction L. In addition, the implantable electrode 1 is shown with a connection portion 22 for connection of the electrode 1 to a medical device.

The electrode 1 is also illustrated with a core 23. The core 23 can be provided for production of the coiling of the connection portion 6. By way of example, the casing 5 can be wound around the core 23 in the region of the connection portion 6 and, therefore, the core 23 can be provided as a winding mold. Once the coil connection portion 6 has been shaped, the core 23 can remain in the connection portion 6. Alternatively, the core 23 can be removed from the coiled connection portion 6. By way of example, when the connection portion 6 is also permanently coiled without the core 23, it may be that the core 23 is no longer necessary. If, however, the core 23 should remain in the connection portion 6, it can be advantageous when the core 23 is fastened non-displaceably to the contact portion 2, to the connection portion 6 and/or to the connection portion 22. The core 23 can be flexible transversely to and along the longitudinal direction L in order to enable a bending and a stretching of the electrode 1 transversely to and along the longitudinal direction L.

So as to be able to form the connection portion 6 helically with the aid of the core 23 or also without a core 23, the connection portion 6 can be wound into the shown form and then thermally treated and, in particular, heated. The heating results in a reduction of stresses in the mechanically wound and held connection portion 6. After cooling, the mechanically wound connection portion 6 can remain in the wound form.

FIG. 9 shows a further exemplary embodiment of the electrode 1 according to the present invention. The same reference signs are used for elements which correspond in terms of form and/or function to elements of the previous exemplary embodiments. One skilled in the art will appreciate that merely the differences from the exemplary embodiment of FIG. 6 will be discussed hereinafter for the sake of brevity.

The electrode 1 is illustrated without the core 23, which is possibly provided optionally. The connection portion 6 is also arranged in a body 24 which can be injected or cast around the connection portion 6 and possibly around parts of the contact portion 2 and/or of the connection portion 3 adjacent to the connection portion 6. By way of example, the body 24 can be manufactured from a casting compound, for example, silicone. The body 24 is preferably resilient at least in the longitudinal direction L, such that it enables a stretching of the connection portion 6 along the longitudinal direction L. The body 24 can simplify the implantation of the electrode 1 since it provides a smooth outer side 25 running along the longitudinal direction L.

Figure 10:
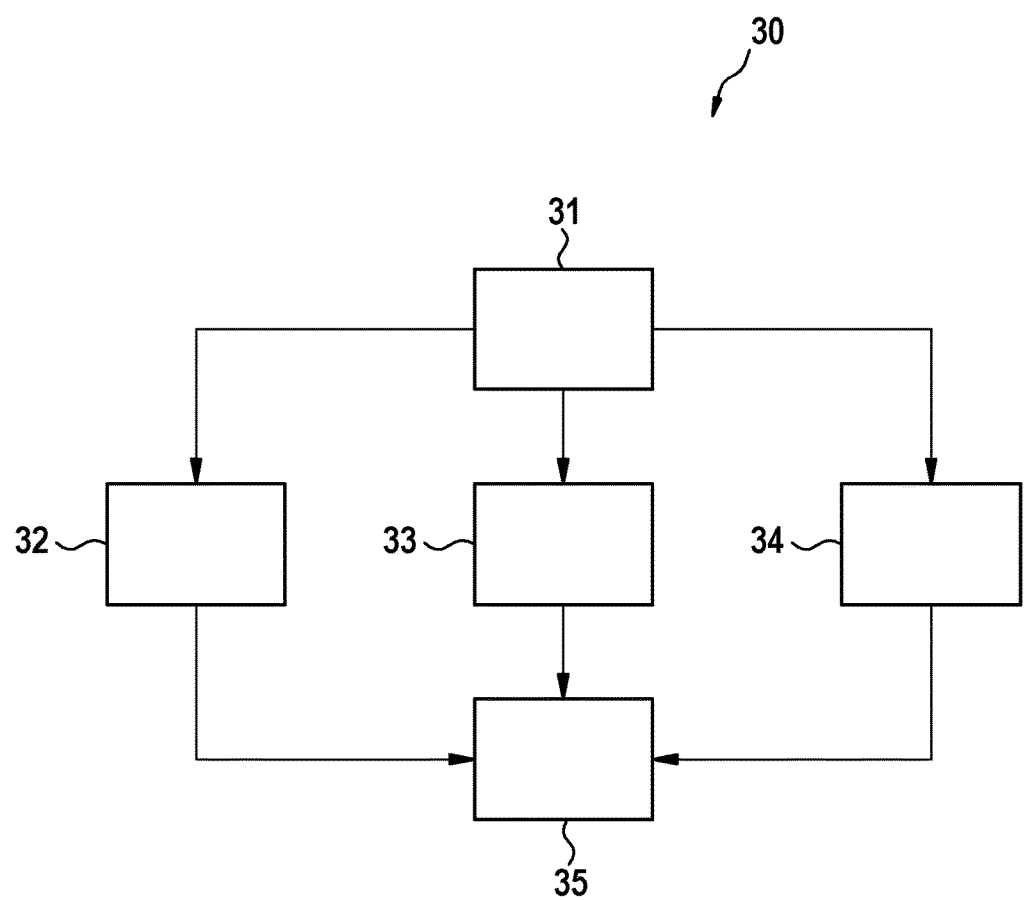
FIG. 10 shows a schematic illustration of an exemplary embodiment of the method according to the present invention for producing the implantable electrode.

FIG. 10 shows the method according to the present invention for producing the implantable electrode 1, schematically as a flow diagram. The same reference signs are used for elements of the previous exemplary embodiments which are helpful in the following explanation of the method.

The method 30 starts with a first method step 31. In the first method step 31, a film 13, 19 can be provided by way of example, wherein the film 13, 19 forms the casing 5 at least of the connection portion 6 or of the electrode 1 as a whole, at least in part. So as to be able to electrically conductively connect at least one connection line 10 to at least one contact element 4, the film 13, 19 can be perforated at a predetermined position in method step 31. By way of example, the film 13, 19 can be mechanically perforated, for example, with a punching tool, with the aid of a laser or a lithography device.

In the method step 31, the contact element 4, the connection line 10, and the plated through-hole 11 connecting the contact element 4 and the connection line 10 can also be formed on the film 13, 19. By way of example, the contact element 4 or the connection line 10 can be provided additively or subtractively on one side of the film 13, 19. The plated through-hole 11 can then be provided in the formed hole. The contact element 4 (previously not formed) or the connection line 10 (previously not formed) can then be provided on the other side of the film 13, 19. The contact element 4 is formed on one side, and the connection line 10 is formed on a side of the film 13, 19 opposite the contact element 4. The hole connects the two sides to one another.

In addition, in method step 31, a further film 13, 19 can be applied to the side of the film 13, 19 on which the connection line 6 is arranged, such that the connection line 6 is embedded not only in part in the film 19, but is embedded completely in the casing 4 between the films 13, 19. The further film 13 can form an inner side of the casing 4.

A method step in which at least the connection portion 6 of the electrode 1 is coiled and, for example, is shaped in a helical manner follows the method step 31. In the method step 32, possibly following the method step 31, the connection portion 6 is on one side stretched to a greater extent than on another side, which, in particular, is opposite. At least the side of the connection portion 6 stretched to a greater extent can be heated optionally during this process.

The stretching can be implemented by pulling on the side to be stretched to a greater extent and, for example, by pulling on the film 19. The electrode 1 and, in particular, the connection portion 6 thereof, for example, with the film 13, can optionally be pressed against a stretching tool 20 and in the process drawn over the stretching tool 20 so as to stretch at least the connection portion 6 to a greater extent on one side. At least the connection portion 6 can also be brought into a hollow-cylindrical form and for this purpose can be wound, for example, around the core 23. The connection portions 6 can be held and tempered in the hollow-cylindrical form in order to relieve any stresses created by the winding of the connection portion 6. The connection portion 6 or the electrode 1 can then be cooled. After cooling, at least the connection portion 6 remains in the wrapped or wound form.

Instead of being followed by the method step 32, the method step 31 can also be followed optionally by the method step 33. In the method step 33 at least the connection portion 6 of the electrode 1 is wound helically and then fixed in the helical form, for example, by fastening to the core 23.

Alternatively or additionally to being followed by one of the method steps 32 and 33, the method step 31 can be followed by the method step 34. In the method step 34, at least one side, for example, the outer side 7 and/or the inner side 9 of the casing 5, i.e., for example, the film 19 or the film 13 is provided with a coating, wherein the coating exerts a mechanical stress onto the casing of the connection portion 6. On account of the mechanical stress, the connection portion 6 curves into the helix form. If the coating is arranged on the outer side 7, said coating can exert a compressive stress. A coating arranged on the inner side 9 can exert a tensile stress.

Each of method steps 32, 33, 34 can be followed by the method step 35, in which the method 30 is completed.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

LIST OF REFERENCE NUMERALS

1 implantable electrode
2 contact portion
3 contact side
4 contact element
5 casing
6 connection portion
7 outer side
8 narrow side
9 inner side
10 connection line
11 plated through-hole
12 semi-finished product 13 film
14, 15 groove
16, 17, 18 portions of the film
19 film, stretched
20 stretching tool
21 edge
22 connection portion
23 core
24 body
25 outer side of the body
30 method
31 start
32 stretching
33 winding and optional fastening
34 coating
35 end
A longitudinal axis
B width direction
D longitudinal direction of the contact portion
K1, K2 force arrow
L longitudinal direction of the connection portion
W angle

We claim:

1. An implantable electrode comprising:
   at least one contact element for contacting bodily tissue;
   a connection portion comprising at least one connecting line for connecting a medical device to the at least one contact element; and
   a cylindrical core,
   wherein the cylindrical core is flexible along a longitudinal axis of the electrode,
   wherein the connection portion is wound around the core and individual turns, or all turns, in the wound form of the cylindrical portion are fastened to the core, and
   wherein the connection portion is formed flat and the at least one connecting line is embedded in the flat connection portion,
   wherein the at least one connecting line is arranged between two electrically insulating thermoplastic polymer films which are permanently connected to one another,
   wherein a first of the two films is planer and has the at least one contact element formed on one of its sides and the at least one connecting line formed on a side of the first film opposite the at least one contact element,
   wherein a second of the two films is planar and is connected to the first film on the one side of the first film where the at least one connecting line is formed,
   wherein the first and second films forming the connection portion are wound around the core.

2. The implantable electrode according to claim 1, wherein the connection portion is helical, at least in one or more portions.

3. The implantable electrode according to claim 1, wherein the connection portion is formed as a flat ribbon wound around the longitudinal axis.

4. The implantable electrode according to claim 1, wherein the connection portion has broad and narrow sides, wherein one of the broad sides is an outer side pointing away from the longitudinal axis.

5. The implantable electrode according to claim 4, wherein the connection portion has an inner side facing towards the longitudinal axis, wherein the inner side is smaller than the outer side.

6. The implantable electrode according to claim 5, wherein the outer side is stretched to a greater extent than the inner side.

7. The implantable electrode according to claim 5, wherein the outer side has been mechanically extended and at the same time thermally treated.

8. The implantable electrode according to claim 1, wherein the connection portion is provided with a coating exerting a mechanical stress onto the connection portion.

9. The implantable electrode according to claim 1, wherein the electrode is embodied with a contact portion comprising the contact element, wherein the contact portion is substantially flat.

\* \* \* \* \*